United States Patent
Stone et al.

(10) Patent No.: US 10,016,183 B2
(45) Date of Patent: Jul. 10, 2018

(54) BIOPSY SPECIMEN CARRIER

(71) Applicant: 3D Biopsy LLC, Vail, Vail, CO (US)

(72) Inventors: Nelson N. Stone, Vail, CO (US); David A. Schechter, Longmont, CO (US); Samuel V. Verplanck, Boulder, CO (US); Mike A. Brown, Thornton, CO (US); J. Louis Kovach, Lewis Center, OH (US); Dean M. Kingston, Arvada, CO (US)

(73) Assignee: 3DBiopsy, Inc., Aurora, CO (US)

( * ) Notice: Subject to any disclaimer, the term of this patent is extended or adjusted under 35 U.S.C. 154(b) by 22 days.

(21) Appl. No.: 15/292,161

(22) Filed: Oct. 13, 2016

(65) Prior Publication Data

US 2017/0100103 A1    Apr. 13, 2017

Related U.S. Application Data

(60) Provisional application No. 62/241,003, filed on Oct. 13, 2015.

(51) Int. Cl.
| | |
|---|---|
| *G01N 1/10* | (2006.01) |
| *A61B 10/00* | (2006.01) |
| *G01N 1/28* | (2006.01) |
| *G01N 1/31* | (2006.01) |

(52) U.S. Cl.
CPC ........... *A61B 10/0096* (2013.01); *G01N 1/28* (2013.01); *G01N 2001/315* (2013.01)

(58) Field of Classification Search
CPC ........................................................ G01N 1/00
See application file for complete search history.

(56) References Cited

U.S. PATENT DOCUMENTS

| | | | | | |
|---|---|---|---|---|---|
| 4,486,536 | A | * | 12/1984 | Baker .................. | G01N 33/726 422/411 |
| 4,645,743 | A | * | 2/1987 | Baker ..................... | C12Q 1/28 422/421 |

* cited by examiner

*Primary Examiner* — Jyoti Nagpaul
(74) *Attorney, Agent, or Firm* — Mueller Law, LLC; Jerry K. Mueller, Jr.

(57) ABSTRACT

Disclosed is a biopsy specimen carrier adapted for tissue biopsy samples where the specimen need not be removed or handled once housed within and including a backer board, a media removable secured to the backer board, a media carrier removable secured to the media and receptive to hold a tissue biopsy sample, a first strip of adhesive material on the media adjacent to the media carrier, and a release strip covering the first strip of adhesive material. The media is foldable to cover the media carrier carrying a tissue biopsy sample and is secured to the first strip of adhesive material with the release strip removed.

20 Claims, 10 Drawing Sheets

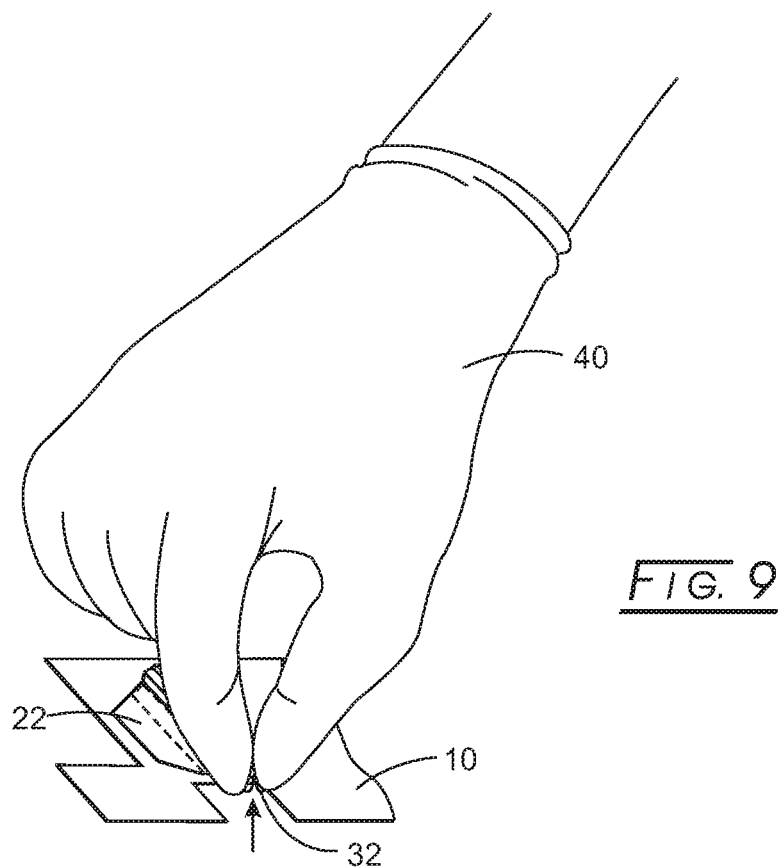
FIG. 9
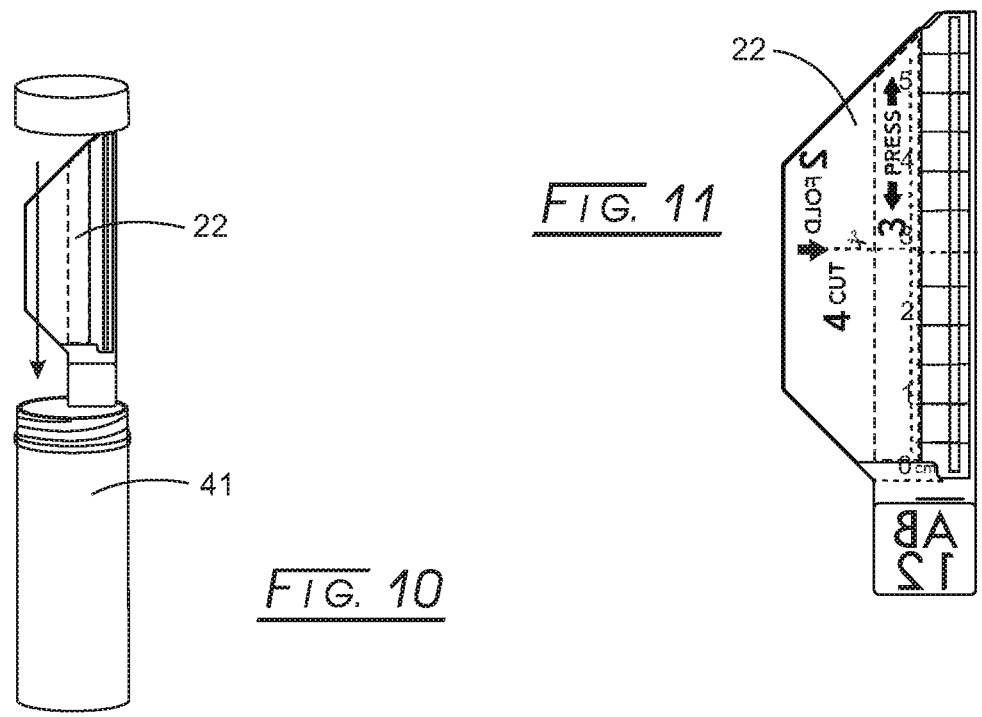
FIG. 10
FIG. 11

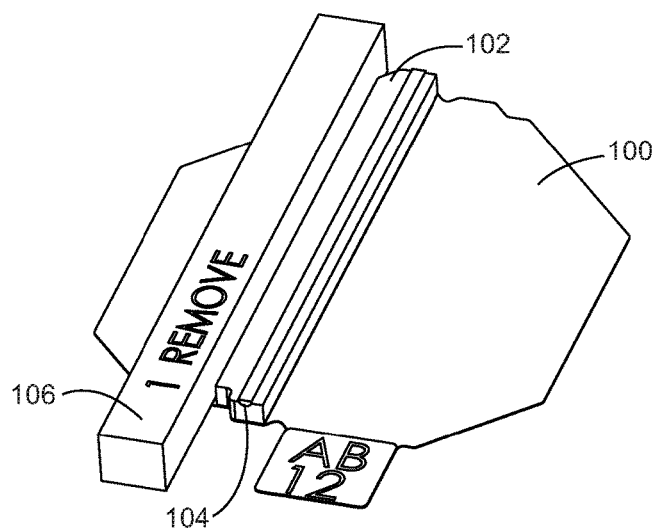
FIG. 24
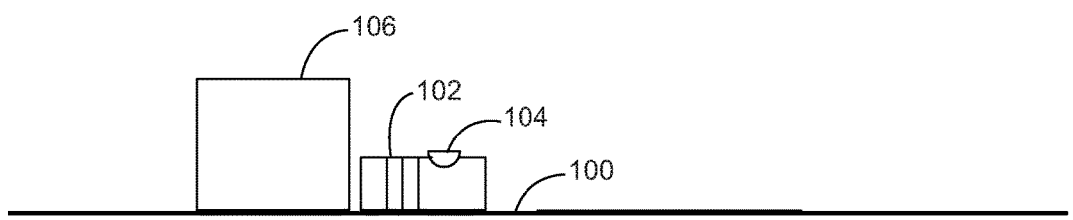
FIG. 25
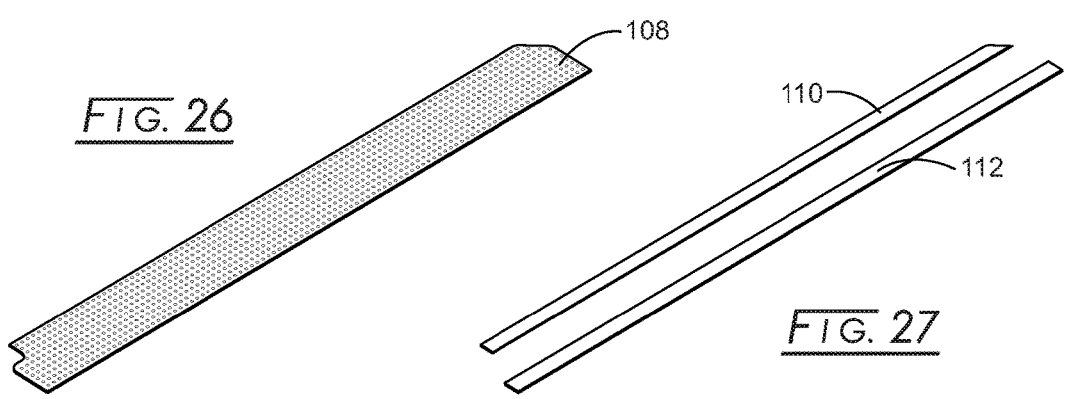
FIG. 26
FIG. 27

BIOPSY SPECIMEN CARRIER

CROSS-REFERENCE TO RELATED APPLICATIONS

This application claims benefit of provisional application Ser. No. 62/241,003 filed Oct. 13, 2015.

STATEMENT REGARDING FEDERALLY SPONSORED RESEARCH AND DEVELOPMENT

Not applicable.

THE NAMES OF THE PARTIES TO A JOINT RESEARCH AGREEMENT

Not applicable.

REFERENCE TO A "SEQUENCE LISTING," A TABLE, OR A COMPUTER PROGRAM

Not applicable.

STATEMENT REGARDING PRIOR DISCLOSURES BY THE INVENTOR OR A JOINT INVENTOR

Not applicable.

BACKGROUND OF THE INVENTION

The present disclosure relates to biopsy specimen carriers and more particularly to a biopsy specimen carrier adapted for prostate biopsy samples where the specimen need not be removed or handled once housed within.

There is a need to process biopsy samples through histology while maintaining orientation and integrity of the tissue sample such that a three dimensional (3D) map of tissue pathology can be accurately recreated. Biopsy samples, such as prostate tissue, are fragile, friable, and sometimes fragmented. It is critical to maintain and map orientation, such as distal/proximal and anterior/posterior ends, and the relative length of the tissue in order to accurately diagnose and map pathological changes in the tissue. There is a significant need to maintain sample integrity and reduce handling of the tissue sample during processing. Additionally, some biopsy samples may be too long to fit in a standard tissue-processing cassette. Currently, biopsies are placed on a foam biopsy sponge then placed in cassette to go through standard histopathological processing. During this process, the tissue can be damaged and orientation may be lost. There is a need to reduce biohazard and specimen providence errors (3% of samples).

For example, U.S. Pat. No. 7,888,132 discloses, in part, a histological specimen retaining device for processing tissue having a permeable target 14 on a permeable sheet 12 where the tissue sample is placed on target 14 and extended flap portions 16a-d are folded over target 14 forming a packet 26 for retaining the tissue sample and processing the tissue and packet using known histological preparation and embedding methods. Target 14 includes measurement marking lines 24 for showing the size of the tissue specimen.

Despite the presence of histological specimen devices in the art, there exists a need for improving such devices, and it is to such an improved biopsy carrier that the present disclosure is addressed.

BRIEF SUMMARY OF THE INVENTION

For present purposes, a few definitions are in order:
Media: The material that is in direct contact with the biopsy sample.
Media Carrier: The material that holds the media in place.
Backer Sheet: The material that holds pre-labeled media carriers in an organized manner. Sometimes referred to as a backer board herein.

Disclosed is a biopsy specimen carrier adapted for tissue biopsy samples where the specimen need not be removed or handled once housed within and including a backer board, a media removable secured to the backer board, a media carrier removable secured to the media and receptive to hold a tissue biopsy sample, a first strip of adhesive material on the media adjacent to the media carrier, and a release strip covering the first strip of adhesive material. The media is foldable to cover the media carrier carrying a tissue biopsy sample and is secured to the first strip of adhesive material with the release strip removed.

Also disclosed is a method for using the disclosed biopsy specimen carrier. The tissue biopsy sample is placed on the media carrier. The release strip is removed from the first strip of adhesive material. The media is folded in half to capture the tissue biopsy sample between the folded media with the first strip of adhesive material securing the folded media. The folded media now can be removed from the backer board and placed into a fixative solution. Thereafter, it can be cut in half and each half placed into a tissue cassette.

BRIEF DESCRIPTION OF THE SEVERAL VIEWS OF THE DRAWINGS

For a fuller understanding of the nature and advantages of the present method and process, reference should be had to the following detailed description taken in connection with the accompanying drawings, in which:

FIG. 9 shows a person removing the media carrier from the backer board;

FIG. 10 shows the removed media carrier being placed in a vial of fixing solution (formalin);

FIG. 11 shows the printed information on the folded media carrier;

FIG. 24 shows an isometric view of alternative embodiment;

FIG. 25 is an end view of the alternative embodiment of FIG. 24;

FIG. 26 is an isometric view of a perforated adhesive layer;

FIG. 27 is an isometric view of a discontinuous adhesive layer;

The drawings will be described in greater detail below.

DETAILED DESCRIPTION OF THE INVENTION

Figure 1:
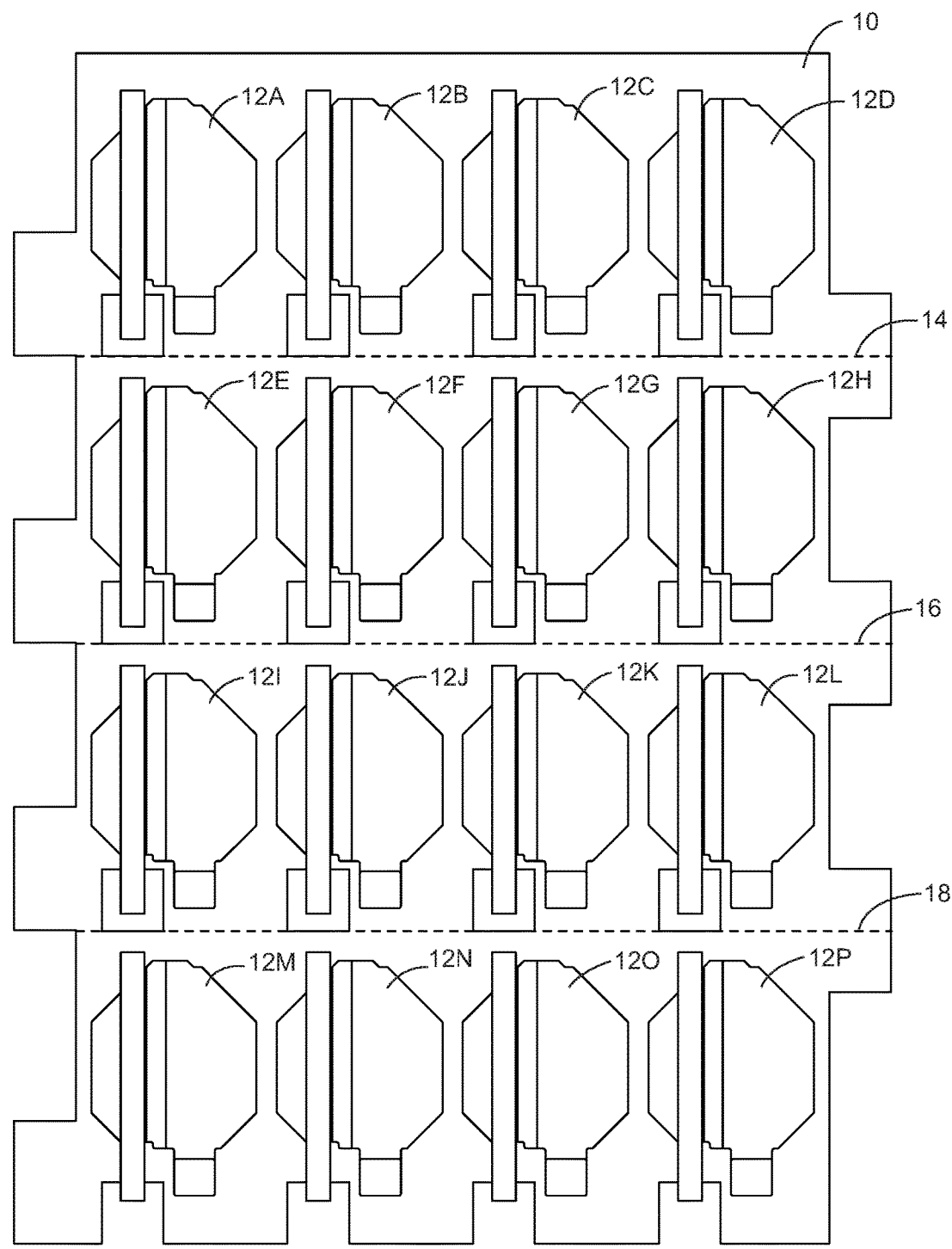
FIG. 1 is a layout of the prostrate biopsy carriers on a backer board.

FIG. 1 shows a backer board, 10, holding 4 rows of media carriers, 12A-12P, which are arranged in adjacency. It should be understood that the number of rows of media carriers could be greater or lesser in number. The same is true for the number of media carriers present in each row. The number of media carriers shown in FIG. 1 is for illustrative purposes and does not constitute a limitation of the present disclosure. It will be observed that separation lines, 14-18, are present on backer board 10 between each of the rows of media carriers to enable each row of media carriers to be separated and retained on sections of media carrier 22.

Figure 2:
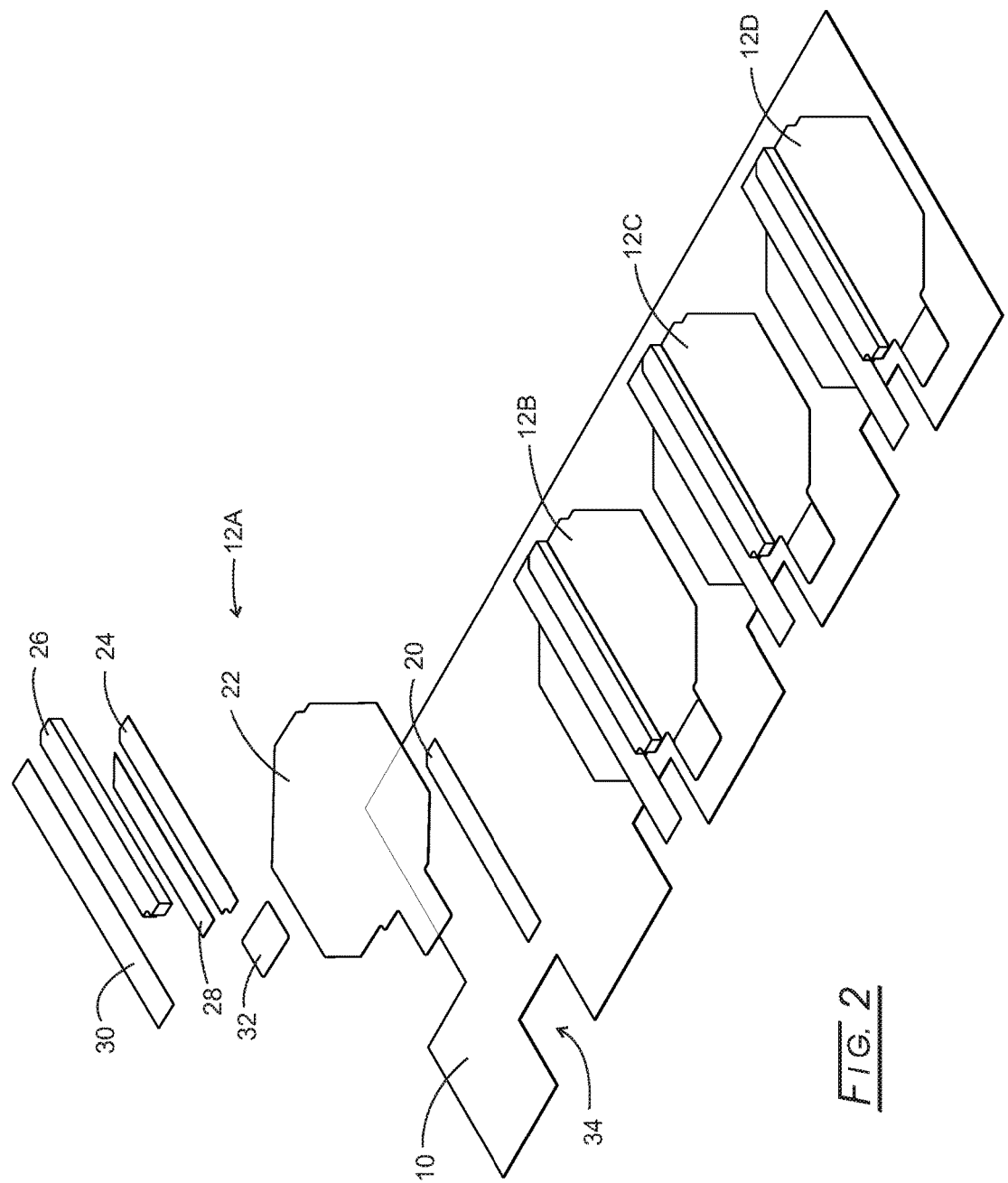
FIG. 2 is an isometric view of one of the prostrate biopsy carriers of FIG. 1 with the individual components of one of the carriers being shown in an exploded view.

The top row of media carriers 12A-12D and shown separated from the other media carriers in FIG. 2. Additionally, media carrier 12A is shown in an exploded view to show the various components of media carrier 12A and the other media carriers in FIG. 1. An adhesive strip, 20, on backer board 10 holds a media carrier sheet, 22, in place. Adhesive strip 20 could be adhesive material laid down on backer board 10 or it could be a piece of double-sided tape. Another adhesive strip, 24, holds a media, 26, in place and affixed to media carrier sheet 22. Again, adhesive strip 24 could be adhesive material laid down on media carrier sheet 22 or a strip of double-sided tape. Desirably, adhesive strip 20 is located directly below media 26. Adjacent to media 26 is yet a third strip of adhesive, 28, located on media carrier sheet 22 and covered by a release strip, 30. Finally, a reinforcing tab, 32, is located adjacent to media carrier sheet 22.

It will be observed that backer board 10 has a notch, 34, for release strip 30 to extend into for facilitating its removal. Each section of backer board 10 supporting a media carrier has a similar notch for the same purpose, as will be more fully explained below. Backer board 10 could be made of, for example, polyester (e.g., polyester terephthalate or PET), polycarbonate, and like materials.

Figure 3:
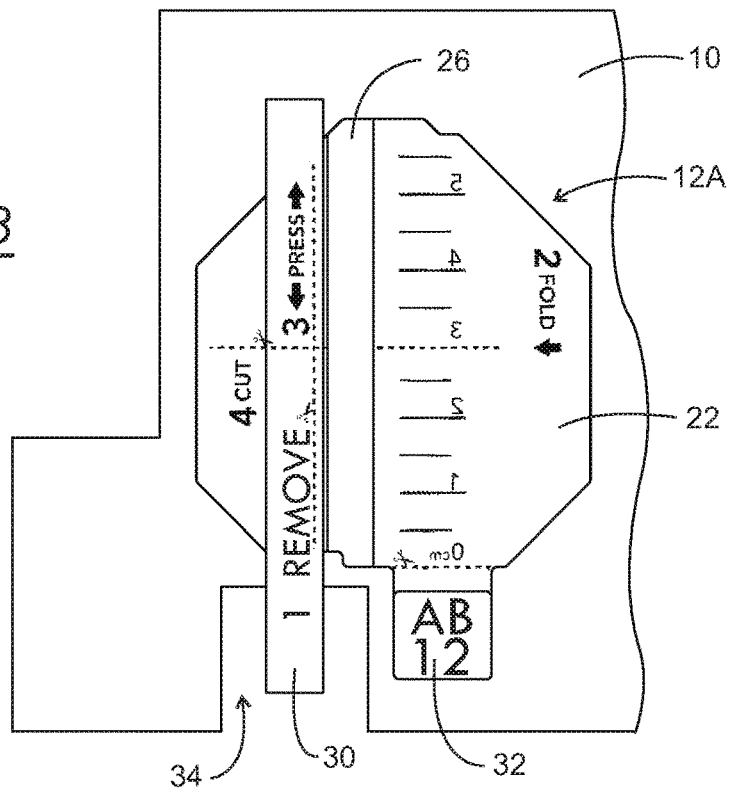
FIG. 3 is one of the prostrate biopsy carriers that has been separated from the other carriers.
Figure 4:
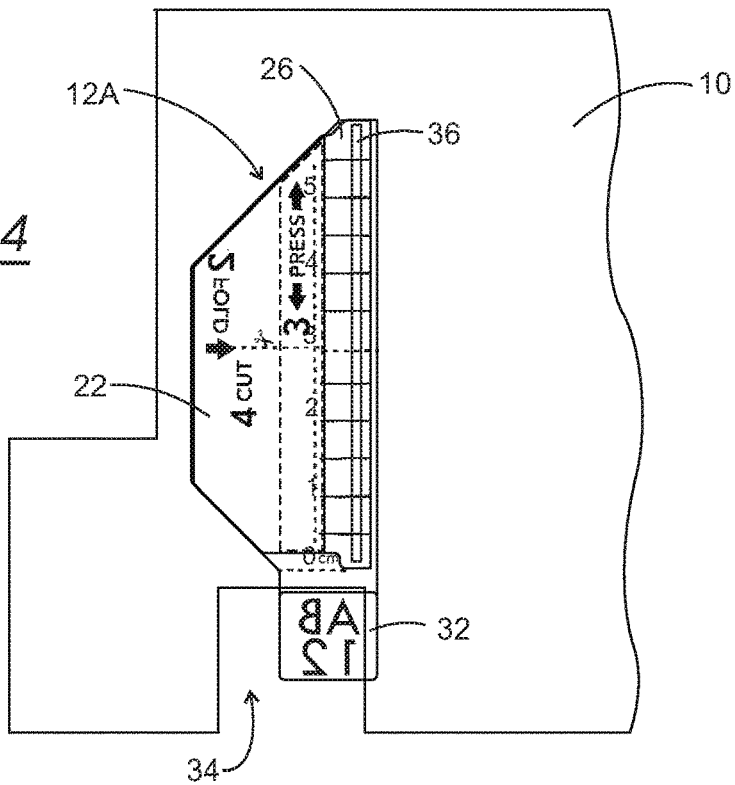
FIG. 4 is the individual prostrate biopsy carrier of FIG. 3 folded in half to trap the tissue sample.

In FIG. 3, the printed instructions and ruled measurements are present. They were omitted in the earlier figures for description and understanding purposes. However, media carrier 22 and release strip 30 in FIG. 3 are seen to have instructions for use. In particular, step 1 is printed on release strip 30 and is "REMOVAL". Release strip 30 extends into notch 34 for a person to easily grasp it for its removal. Step 2 is seen on the right side of media carrier 22 and is "FOLD". Step 3 also is located on release strip 30 and is "PRESS" to remind the user to press the right side of media carrier 22 onto adhesive strip 28 when media carrier 22 is folded for trapping the tissue specimen in place. Located opposite Step 2 is Step 4, which is "CUT", and indicates where media carrier 12A is to be cut in half.

Suitable adhesives could be solvent based or water based (hydrophilic). They could be ultraviolet radiation (UV) cured. They could be, for example, a rubber or resin, an acrylic, a silicone, or like adhesive composition. Various of the adhesive layers could discontinuous, strips on either side, and could contain gaps, holes, perforations, or other design to permit pass through of fluids. Additionally, the adhesive could be biocompatible.

It should be noted that media carrier 22 is transparent and may be made from filtration grade spun bonded polyester of about 0.0122" (about 0.03099 mm) in thickness with a weight of about 2.1 oz/yd$^2$ (about 71.2021 g/m$^2$). By being transparent, the user can read the instructions and measurement indicators even when it is folded in half. It will be observed further that tab 32 contains a sample number for unique identification of the tissue biopsy sample. Measurement or geometric indicators indicate distal and proximal orientation of the tissue sample between each half and within each half of media carrier 22.

Media 26 could be made from two different colored materials to distinguish between the distal half and the proximal half of the tissue biopsy half and such color may be transferred to the sample. Such color could be premarked with tissue dye that is actuated by the processing using, for example, encapsulated colorant in the media. Two different color dyes maybe used placed at the proximal end, distal end, and/or and at the middle of the media. Media 26 can be sliced on a microtome without fragmentation and is easily sliced. Media 26 retains the biopsy sample throughout fixation, tissue processing, embedding, slicing, staining, and cover slipping. Moreover, it does not chemically harm the sample, does not interfere with viewing the tissue on a slide, and is permeable. Media 26 could be made from needle-punched polyester about 0.050 inches (about 1.27 millimeters) in thickness and of about 3.5 oz/yd$^2$ (about 118.67 g/m$^2$) in weight. Media 26 also could be made from polypropylene, borosilicate, glass-based media, or other woven or non-woven polymers. Its thickness could range from about 0.030 inches to about 0.160 inches (from about 0.762 millimeters to about 4.064 millimeters) with a weight range of from about 3.0 oz/yd$^2$ to about 12.0 oz/yd$^2$ (from about 101.717 g/m$^2$ to about 406.869 g/m$^2$). Media 26 also could be tinted, calendared or grooved to hold a biopsy sample. Additionally, media 26 could be chemically modified, such as by oxidation or hydroxylation to improve biopsy sample retention.

Media carrier 22 also could be made from polyester, polypropylene, borosilicate, glass bead, and woven and non-woven polymers. It should be resistant to chemicals and can range in thickness from about 0.0045 inches to about 0.0209 inches (from about 0.1143 millimeters to about 0.53086 millimeters) and have a weigh range from about 0.4 oz/yd$^2$ to about 4.0 oz/yd$^2$ (from about 13.5623 g/m$^2$ to about 135.623 g/m$^2$).

Media carrier 22 further could be chemically treated via oxidation with, for example, hydrogen peroxide, and subsequently washed to improve hydrophilic character. The medium additionally could be scored, ultrasonically or mechanically, to form a channel or ridge to assist the transfer and maintenance of the specimen geometry on the media. The medium could be formed of other polymers, as recited above, which other polymers have the characteristics of the cited polymers in regard to their mechanical and optical properties. The media could be pretreated with saline solution to assist in preserving specimen geometry after transfer.

The carrier additionally could be printed with a numeric or alphanumeric code or multiple such codes. Such codes could be human readable, machine readable, or both. One of such multiple codes could be removable and used to document the link between the carrier and the location from the biopsy specimen was taken. An RFID (radio frequency identification) tag could be placed on the carrier backer board. Such tag could be embedded with additional information regarding the carrier and its use.

Figure 5:
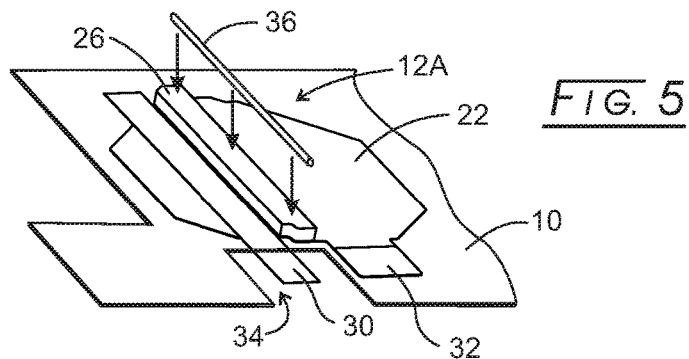
FIG. 5 shows a biopsy sample being placed on the media.
Figure 6:
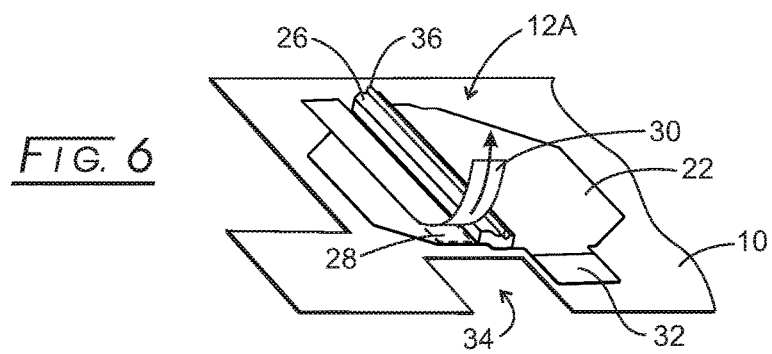
FIG. 6 shows a release strip being removed from a strip of adhesive.
Figure 7:
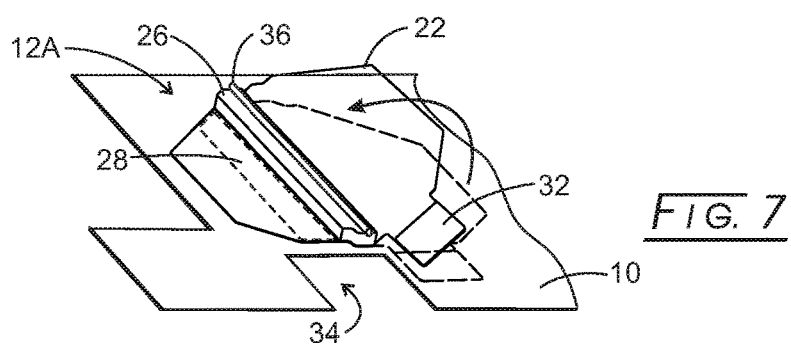
FIG. 7 shows the media carrier being folded in half to a the tissue specimen.
Figure 8:
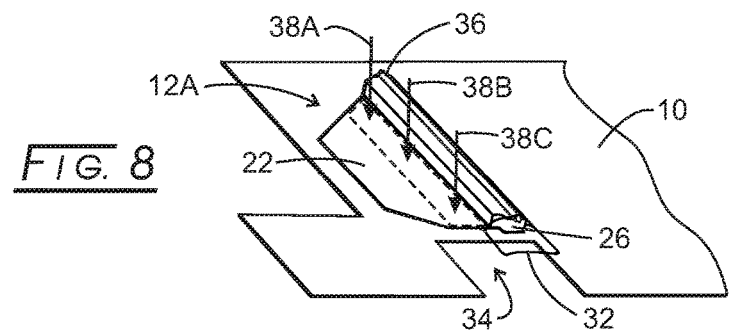
FIG. 8 shows force arrows where pressure is to be applied to keep the media carrier in the folded position.

Returning to the drawings, in FIG. 5 a biopsy sample, 36, is placed onto media 26 for its retention. In FIG. 6, release strip 30 is pulled away. It will be observed that notch 34 enables the user to easily grasp release strip 30. In FIG. 7, backer board 10 is folded in half to trap sample 36. Force arrows, 38A-38C, show where the user should press to ensure that the top folded media carrier 22 is securely held to adhesive strip 28.

In FIG. 9, the user's hand, 40, grasps tab 32 so that media carrier 22 can be pulled away from backer board 10. Media carrier, then, is placed into a vial, 41, of fixative solution (e.g., formalin). In all steps, folded media carrier 22 securely holds the biopsy sample with no handling thereof. FIG. 11 illustrates folded media carrier 22 with all of the lettering present. Again the lettering was absent in the preceding figures so as to not distract from the steps being illustrated.

Figure 12:
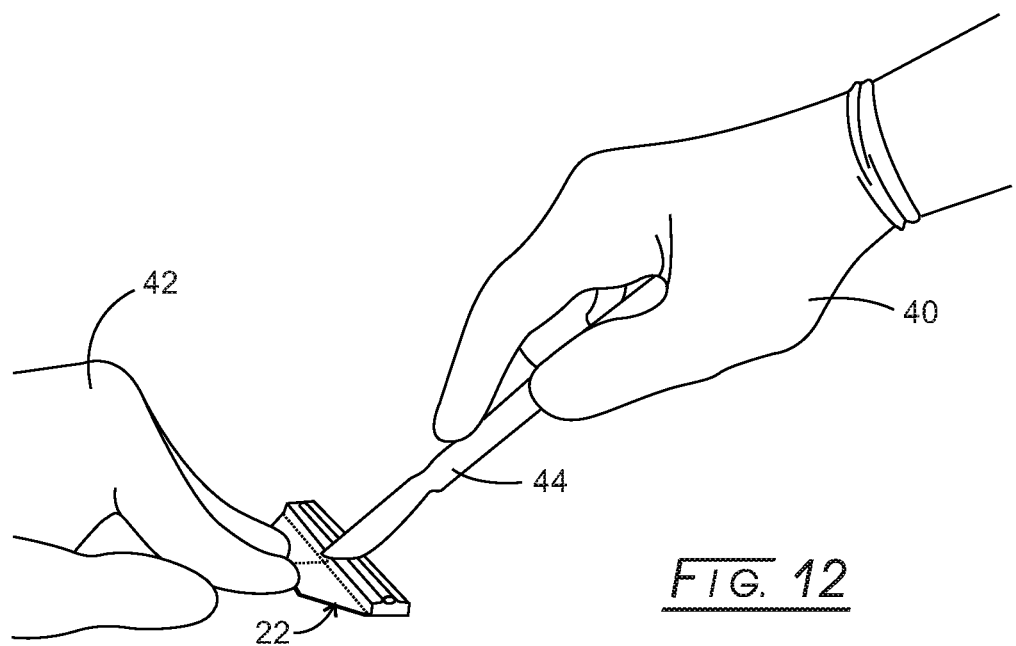
FIG. 12 shows the folded media carrier being cut in half.
Figure 13:
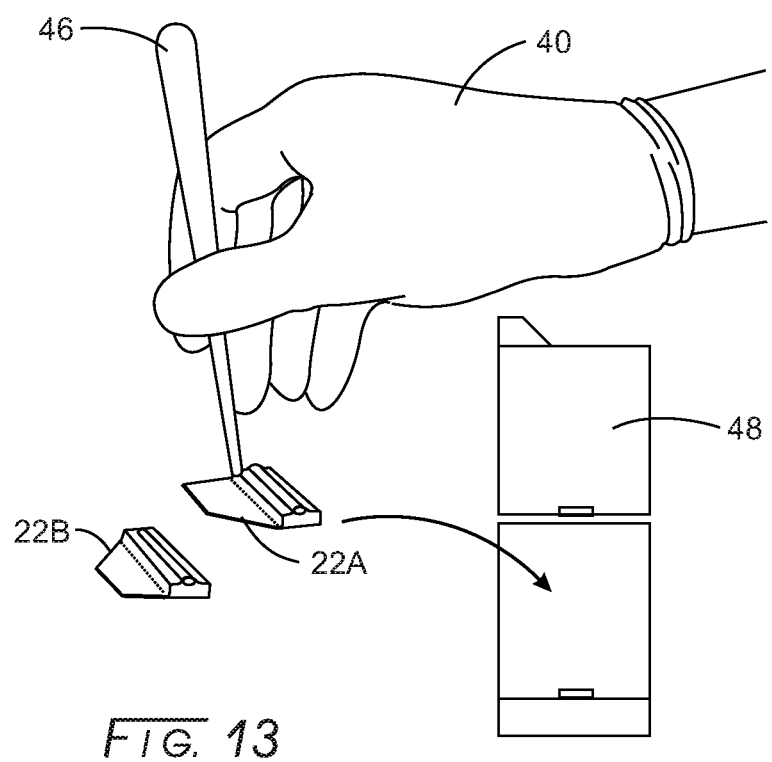
FIG. 13 shows the cut folded media carrier being placed into a tissue cassette.

In FIG. 12, user's hands 40 and 42 hold folded media carrier 22 steady for cutting it in half along the "CUT" line with a scalpel, 44, or other cutting instrument. In FIG. 13, one of the cut media carrier halves, 22A, is picked up with a pair of tweezers, 46, or similar device for its placement into a cassette, 48. The other media carrier half, 22, similarly can be placed into a separate cassette.

The media could be modified using various techniques to assist in the transfer of the biopsy specimen from the biopsy needle to the media by physically cutting or slicing of the media, forming a shape using ultrasonic, heat, or a laser. Such shape could be a channel, L-shaped or L-stepped, grooved, offset groove, or other alteration. Different media materials could be used in order to create a physical feature, such as, for example, a step, L-shape, or channel in the transfer of the biopsy specimen from the biopsy needle to the media.

The unit of measure for the media is Denier (D) and the media could range from about 1 D to about 20 D. The following materials have been effective in testing:

FIN05989: PET 4 oz, 100% 3 D;

WEB04303: PET 3.25 oz, 50% 3 D, 50% 1.5 D;

FIN04785: PP 2.8 oz, 100% PP 2.5 D;

FIN23538: PET 2.8 oz, 100% 3 D;

Superior Felt Style #106100 PET 6 oz, 100 thick, 100% 3 D;

Superior Felt Style#11004 PET 4 oz×36"×0.075 thick, 50% 3 D, 50% 6 D;

and

Superior Felt Style#103.5050-40 PET 3.5 oz×40"×0.050 thick, 100% 3 D.

Figure 14:
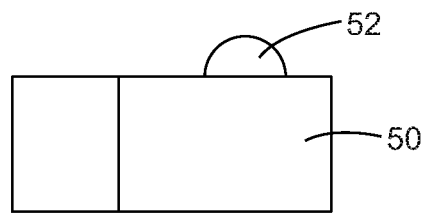
FIG. 14 shows an end view of media supporting a biopsy sample.
Figure 15:
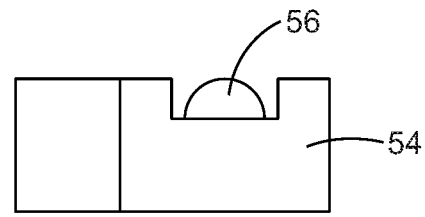
FIG. 15 shows an end view of media having a slot for the biopsy sample.
Figure 16:
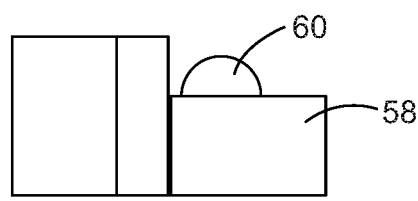
FIG. 16 shows an end view of media formed from two different pieces of different heights.
Figure 17:
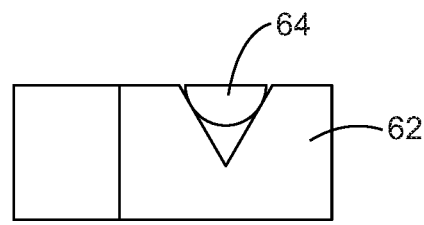
FIG. 17 shows an end view of media having a V-shaped slot for the biopsy sample.
Figure 18:
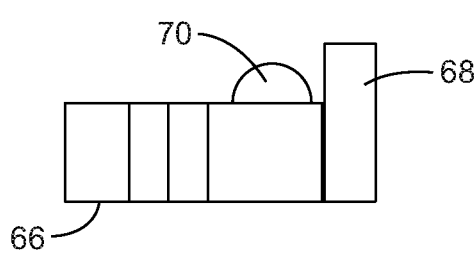
FIG. 18 shows an end view of media formed from two different pieces of different heights.
Figure 19:
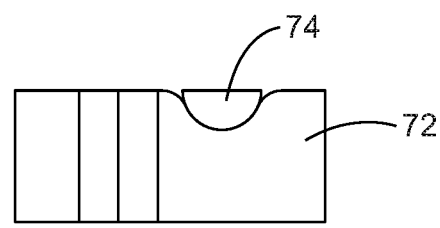
FIG. 19 shows an end view of media having a U-shaped slot for the biopsy sample.
Figure 20:
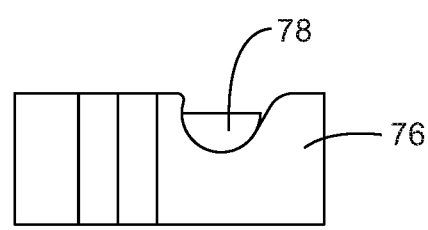
FIG. 20 shows an end view of media having a different U-shaped slot for the biopsy sample.
Figure 21:
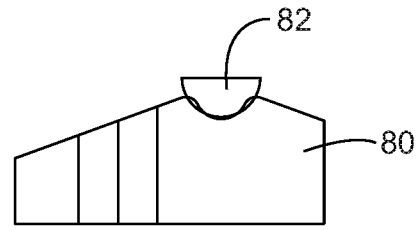
FIG. 21 shows an end view of media formed from two different sloped pieces.

FIGS. 14-21 illustrate these features. In FIG. 14, a media, 50, made of, for example, superior felt, supports a biopsy sample, 52, atop thereof. In FIG. 15, a media, 54, made of, for example, superior felt, has a square shape on one side into which a biopsy sample, 56, is placed. In FIG. 15, a media, 58, made of, for example, superior felt, has its right side lower than the left creating a land upon which a biopsy sample, 58, rests. In FIG. 17, a media, 60, made of, for example, superior felt, has a V-shaped groove on one side and into which a biopsy specimen, 62, is placed. In FIG. 18, a media, 64, made of, for example, superior felt, has an upstanding media, 66, of greater height and made from the same or different material, with media 64 supporting a biopsy sample, 70, adjacent to the higher media 68. In FIG. 19, a media, 72, made of, for example, superior felt, has a semi-circular depression on one side and into which is placed a biopsy specimen, 74. In FIG. 20, a media, 76, made of, for example, superior felt, has a deeper semi-circular depression (different sloped sides) on one side and into which is placed a biopsy specimen, 78. In FIG. 21, a media, 80, made of, for example, superior felt, has two uneven top-sloped top surfaces with a circular depression on the higher sloped top surfaced for supporting a biopsy sample, 82. The skilled artisan will appreciate that additional designs and combinations of media materials could be used in additional to those illustrative designs in the drawings.

The backer board additionally could contain a needle guide. A portion or section of the backer board could be die cut and formed at the proximal position of the carrier. The form could be shaped in various ways to guide the trajectory of the needle/cannula and specimen onto the media. Shapes include, for example, linear, L-shaped, T-shaped, or radial. A current design is simply a slit in the backer board at the centerline of the media from the proximal edge of the backer board to the proximal edge of the media. A crease or score would be added laterally in the backer board at the proximal edge of the carrier. The user could select to manually fold up one side or the other creating a linear guide at the centerline of the media, depending on user preference.

A fixture could be used to register the backer board and, as part of the fixture, provide fixed position needle guides at each position centered on the media at the proximal edge of the carrier. The needle guide could be made with various shapes. For a single position fixture needle guide, a fixture could be used to register the backer board and, as part of the fixture, provide fixed position needle guide. The backer board could be indexed so that the needle guide would be centered on the media at the proximal edge of the carrier. The needle guide could be made with various shapes.

Figure 22:
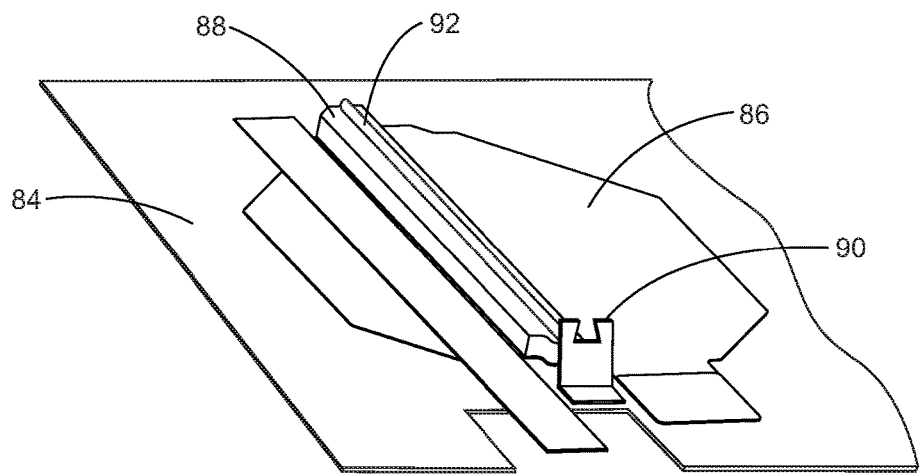
FIG. 22 is an enlarged view of a single alignment fixture for locating the biopsy sample on the media.
Figure 23:
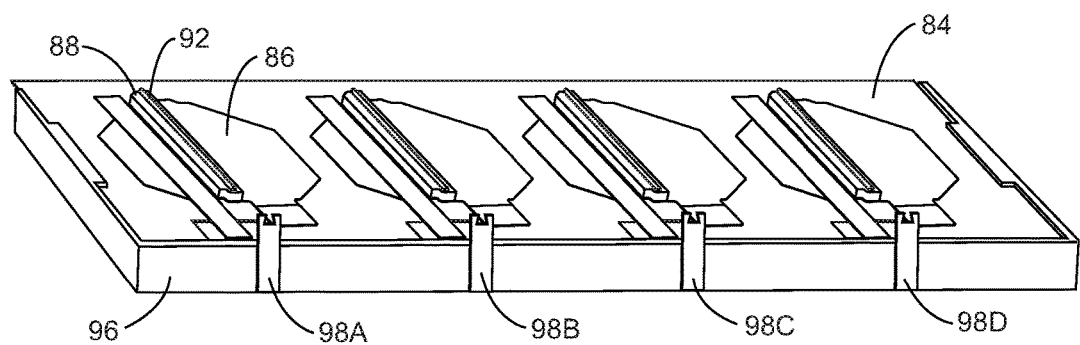
FIG. 23 shows an alignment fixture into which a backer board fits and having 4 openings corresponding with 4 different media for supporting biopsy samples.

FIGS. 22 and 23 illustrate such fixture guides that could be used to locate the biopsy specimen. In particular in FIG. 22, a backer board, 84, carries a media carrier, 86, upon which a media, 88 rests. An alignment fixture, 90, attached to backer board 84 has a trapezoidal cutout into which a biopsy needle can be placed to deposit a biopsy specimen, 92, onto media 88. The cutout shape could be square, rectangular, curvilinear, or the like. Alignment fixture 90 could be affixed to backer board 84 with an adhesive, two-sided tape, or the like. The user inserts the biopsy needle through alignment fixture 90 and pushes the plunger while pulling the biopsy needle outwardly to deposit biopsy specimen 92 onto media 88 at a location determined by the placement of alignment fixture 90.

In FIG. 23, an alignment fixture, 96, carries upstanding alignment segments, 98A-98D. Alignment fixture 96 has side arms with slots designed to receive backer board 84. Backer board 84 carries 4 media carries, only one of which is labeled for ease of illustration. Each of the alignment segments mates with one of the media carriers. Placement of a biopsy specimen proceeds as described in relation to FIG. 22. When all 4 of the media carriers have a biopsy specimen, the backer board is withdrawn so that another backer board can be inserted into alignment fixture 96. It will be appreciated that the end row of media carriers on backer board 10 (see FIG. 1) could be inserted into a similar alignment fixture. The full row of media carriers can be broken off so that the next adjacent row can be fitted into the alignment fixture.

In FIGS. 24 and 25, a media carrier, 100, supports a media, 102, which in turn supports a sample, 104. In this alternative embodiment, however, a removable strip, 106, is made from a thick closed cell foam or similar material and acts as a guide to aid the user in placing specimen 104 onto media 102.

Any adhesive layer disclosed herein could be perforated, as shown in FIG. 26 for an adhesive layer, 108. The perforations could be the same size, different sizes, and/or patterned. Additionally, any adhesive layer disclosed herein could be discontinuous, as shown in FIG. 27 for adhesive layers, 110 and 112. Such discontinuous adhesive layers could be provided in a variety of patterns also.

Figure 28:
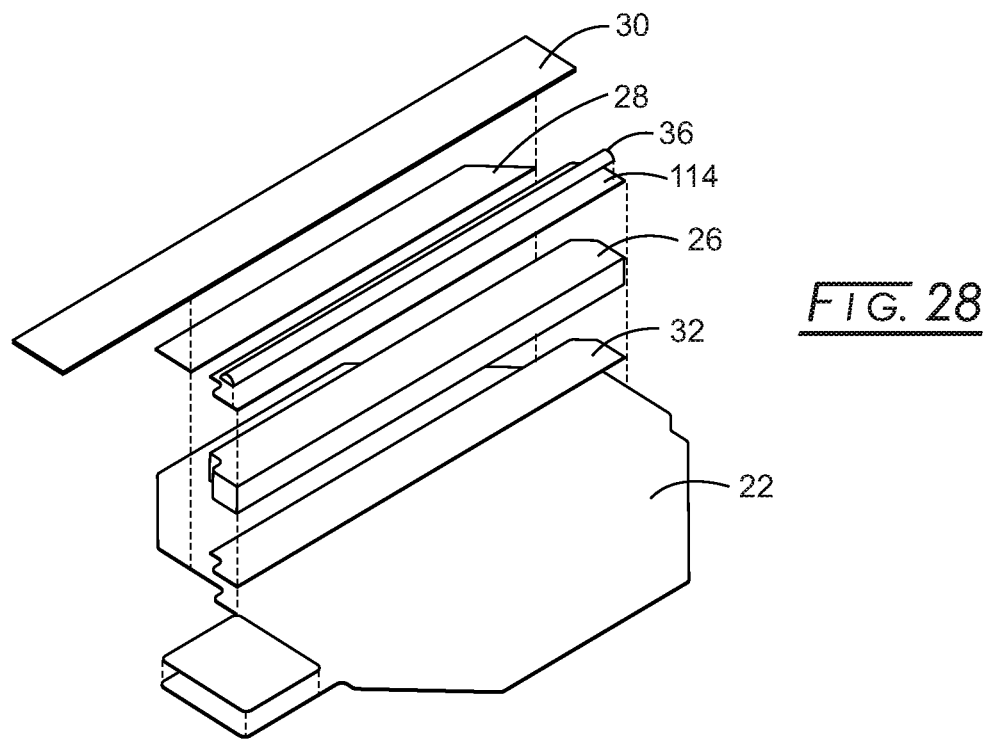
FIG. 28 is an exploded isometric view of yet another alternative embodiment.
Figure 29:
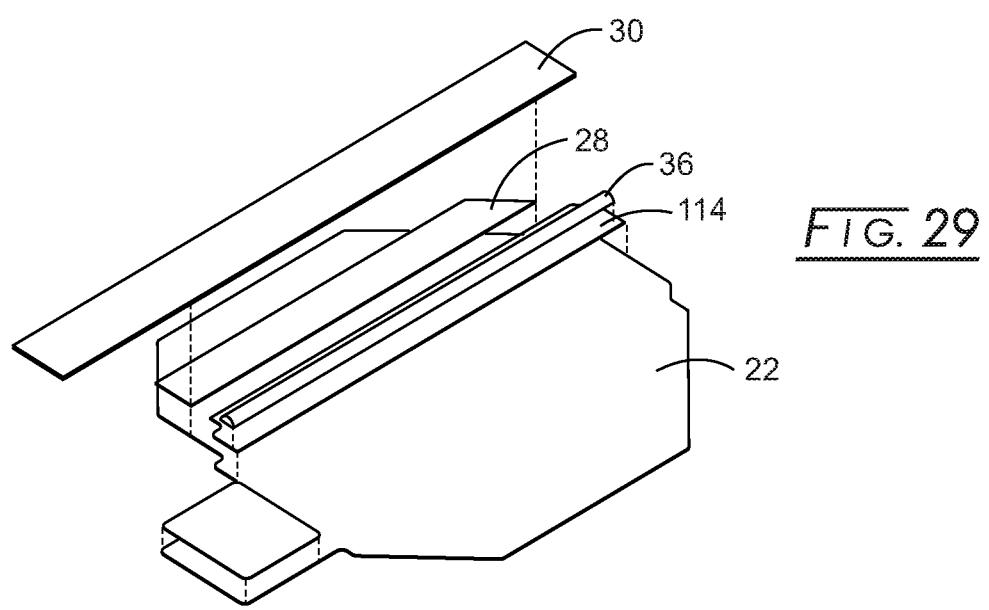
FIG. 29 is an exploded isometric view of yet another a further alternative embodiment.

Referring now to the further embodiment in FIG. 28, the components are numbered according to FIG. 5. The difference here is that an adhesive layer, 114, is used to atop media 26 to secure specimen 36. In FIG. 39, media 26 has been eliminated so that specimen 36 is directed held by adhesive layer 114 onto media support 22. Additionally, a compliant open cell or non-fluid restricting material located between the adhesive and the backer board. Compliance would ensure that the specimen would remain under a light compressive force once the media is folded over and secured.

While the apparatus, system, and method have been described with reference to various embodiments, those skilled in the art will understand that various changes may be made and equivalents may be substituted for elements thereof without departing from the scope and essence of the disclosure. In addition, many modifications may be made to adapt a particular situation or material in accordance with the teachings of the disclosure without departing from the essential scope thereof. Therefore, it is intended that the disclosure not be limited to the particular embodiments disclosed, but that the disclosure will include all embodiments falling within the scope of the appended claims. In this application all units are in the metric system and all amounts and percentages are by weight, unless otherwise expressly indicated. Also, all citations referred herein are expressly incorporated herein by reference.

The invention claimed is:

1. A biopsy specimen carrier adapted for tissue biopsy samples where the specimen need not be removed or handled once housed within, which comprises:
   (a) a backer board;
   (b) a media removably secured to the backer board;
   (c) a media carrier removably secured to the media and receptive to hold a tissue biopsy sample;
   (d) a first strip of adhesive material on the media adjacent to the media carrier;
   (e) a release strip covering the first strip of adhesive material,
   the media being foldable to cover the media carrier carrying a tissue biopsy sample and be secured to the first strip of adhesive material with the release strip removed.

2. The biopsy specimen carrier of claim 1, wherein the media has measurement indicia and instructions for use printed thereon and the release strip has instructions for use printed thereon.

3. The biopsy specimen carrier of claim 2, wherein the media is transparent.

4. The biopsy specimen carrier of claim 3, wherein the media has a cut line printed thereon.

5. The biopsy specimen carrier of claim 2, wherein the measurement indicia notates the tissue biopsy sample distal/proximal and anterior/posterior ends, and the relative length of the tissue biopsy sample.

6. The biopsy specimen carrier of claim 1, with the media carrier holding a tissue biopsy sample.

7. The biopsy specimen carrier of claim 6, where the media has been folded in half.

8. The biopsy specimen carrier of claim 7, where the media has been removed from the backer board.

9. The biopsy specimen carrier of claim 1, wherein the media is removably secured to the backer board with a strip of a second adhesive; and the media carrier is removably secured to the media with a third strip of an adhesive.

10. An array of separable biopsy specimen carrier of claim 1 carried by a backer board.

11. The biopsy specimen carrier of claim 1, wherein the media is formed from two or more sections of different composition.

12. The biopsy specimen carrier of claim 1, wherein an alignment cutout is formed into the media into which the biopsy sample rests.

13. The biopsy specimen carrier of claim 1, wherein an alignment fixture is located adjacent to the media.

14. The biopsy specimen carrier of claim 13, wherein the backer board is captured by the alignment fixture for multiple media.

15. A method for capturing a tissue biopsy sample, which comprises the steps of:
   (a) providing a biopsy specimen carrier adapted for tissue biopsy samples where the specimen need not be removed or handled once housed within, which comprises:
      (i) a backer board;
      (ii) a media removably secured to the backer board;
      (ii) a media carrier removably secured to the media and receptive to hold a tissue biopsy sample;
      (iv) a first strip of adhesive material on the media adjacent to the media carrier;
      (v) a release strip covering the first strip of adhesive material;
   (b) placing a tissue biopsy sample on the media carrier;
   (c) removing the release strip from the first strip of adhesive material;
   (d) folding the media in half to capture the tissue biopsy sample between the folded media with the first strip of adhesive material securing the folded media.

16. The method of claim 15, additionally comprising the step of printing measurement indicia and instructions for use on the media and has instructions for use on the release strip.

17. The method of claim 16, additionally comprising the step of printing a cut line on the media.

18. The method of claim 15, additionally comprising the step of providing an array the biopsy specimen carriers on the backer board.

19. The method of claim 15, additionally comprising supplying an alignment fixture adjacent to the media for aligning placement the biopsy sample on the media.

20. The method of claim 19, additionally comprising supplying an alignment fixture carrying a series of upstanding alignment segments for alignment placement of biopsy samples on a series of adjacent medias.

* * * * *